United States Patent [19]
Butterfield et al.

[11] Patent Number: 6,017,522
[45] Date of Patent: Jan. 25, 2000

[54] SEGMENTED CHELATING POLYMERS AS IMAGING AND THERAPEUTIC AGENTS

[75] Inventors: Dennis E. Butterfield, Rochester, N.Y.; Dennis K. Fujii, Downingtown, Pa.; David L. Ladd, Wayne, Pa.; Robert A. Snow, West Chester, Pa.; Julia S. Tan, Rochester, N.Y.; John L. Toner, Downingtown, Pa.

[73] Assignee: Sterling Winthrop Inc., New York, N.Y.

[21] Appl. No.: 08/845,421

[22] Filed: Apr. 25, 1997

Related U.S. Application Data

[62] Division of application No. 08/221,714, Mar. 31, 1994, Pat. No. 5,730,968.

[51] Int. Cl.⁷ .......................... A61K 31/77; A61K 49/00; A61K 51/00; C08G 65/48
[52] U.S. Cl. ..................... 424/78.37; 424/78.08; 424/78.17; 424/1.65; 424/9.322; 424/9.323; 530/815; 530/816; 525/406
[58] Field of Search .............. 424/78.37, 78.08, 424/1.65, 9.322, 9.323, 78.17; 530/815, 816; 525/406

[56] References Cited

U.S. PATENT DOCUMENTS

| | | |
|---|---|---|
| 3,859,337 | 1/1975 | Herz et al. |
| 4,916,246 | 4/1990 | Felder et al. |
| 5,137,711 | 8/1992 | Weber et al. |
| 5,283,339 | 2/1994 | Arnold. |

FOREIGN PATENT DOCUMENTS

| | | |
|---|---|---|
| 0-326226 | 8/1989 | European Pat. Off. |
| 4017439 | 12/1991 | Germany. |
| WO 91-18630 | 12/1991 | Germany. |

*Primary Examiner*—Edward J. Webman
*Attorney, Agent, or Firm*—Fish & Richardson P.C.

[57] ABSTRACT

A composition suitable for use in diagnostic imaging or as a cell killing agent comprising a chelating residue linked via an amide linkage to a poly(alkylene oxide) moiety, said compisition having a molecular weight of at least 4,500;

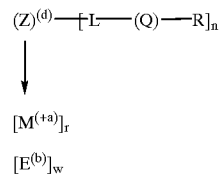

wherein:
  Z is a chelating residue;
  Q is a divalent poly(alkylene oxidylene) moiety having a carbon terminus at R and at L;
  L represents an amide linkage;
  $E^{(b)}$ is one or more counterions each having a charge of b;
  b is an integer from 1, 2 and 3;
  n is an integer selected from the group 1, 2, 3 and 4;
  w is zero or an integer from 1 to 5;
  $M^{(+a)}$ is a cation, having a charge of +a;
  a is an integer from 1 to 4;
  r is 0 or an integer from 1 to 3, provided that when r is 2–3, each $M^{(+a)}$ can be the same or different cation;
  d is the total charge on the chelating residue and is an integer from 0 to 10;
  $d + \Sigma(b \cdot w) + \Sigma(a \cdot r) = 0$; and
  R is a capping moiety chosen from the group consisting of hydrogen, hydroxyl, $C_1$–$C_4$ alkyl, aryl containing 6 to 24 carbon atoms, $C_2$–$C_5$ alkanoyloxyl and $C_1$–$C_4$ alkoxy, or R is an immunoreactive group or cytotoxic drug linked to Q by a chemical bond or a linking group.

7 Claims, No Drawings

SEGMENTED CHELATING POLYMERS AS IMAGING AND THERAPEUTIC AGENTS

This is a divisional of application Ser. No. 08/221,714 filed Mar. 31, 1994 now U.S. Pat. No. 5,730,968.

FIELD OF INVENTION

This invention relates to segmented chelating polymers which are useful as imaging agents and as cytotoxic agents and to their compositions and methods of use.

BACKGROUND OF THE INVENTION

Magnetic resonance (MR) is widely used for obtaining spatial images of multi-celled organisms or bodies for clinical diagnosis. A review of this technology and clinical applications is provided by D. P. Swanson et al, in *Pharmaceuticals in Medical Imagina*, 1990, Macmillan Publishing Company, pages 645–681.

Magnetic resonance images are derived instrumentally as a composite of the effects of a number of parameters which are analyzed and combined by computer. Choice of the appropriate instrument parameter controls, such as radio frequency (Rf), pulsation and timing can be utilized to enhance or attenuate the signals of any of the image-producing parameters to thereby improve image quality and provide better anatomical and functional information. In many cases, magnetic resonance imaging has proven to be a valuable diagnostic tool, inasmuch as normal and diseased tissue, by virtue of their possessing different responses to parameter values, can be differentiated in the image.

In magnetic resonance imaging of the body of a mammal such as a human, an in vivo image of an organ or tissue is obtained by placing at least the portion of the body to be imaged in a strong external magnetic field, pulsing with radio frequency energy, and observing the effect of the pulses on the magnetic properties of the protons contained in and surrounding the organ or tissue. This is especially useful in imaging the circulatory vasculation of the body (i.e. the blood pool). A number of magnetic parameters can be measured. The proton relaxation times, $T_1$ and $T_2$, are of primary importance. $T_1$, also called the spin-lattice or longitudinal relaxation time, and $T_2$, also called the spin-spin or transverse relaxation time, are functions of the chemical and physical environment of the organ or tissue water and are measured using Rf pulsing techniques. This information is analyzed as a function of spatial location by computer which transforms the information to generate an image.

Often the image produced lacks appropriate contrast, e.g., between normal and diseased tissue, reducing diagnostic effectiveness. To overcome this drawback, contrast agents have been used. MR contrast agents are magnetically active substances which exert an effect on the magnetic resonance parameters of nuclei in molecules proximal to them. Theoretically, a contrast agent, if taken up preferentially by a certain portion of an organ or a certain type of tissue, e.g., diseased tissue, can provide a change in contrast or enhancement in the resultant images of that tissue.

Inasmuch as magnetic resonance images are strongly affected by variations in the $T_1$ and $T_2$ parameters, it is desirable to have a contrast agent which effects either or both parameters. Research has focused predominantly on two classes of magnetically active materials, i.e., paramagnetic materials, which act to decrease $T_1$ and $T_2$, and superparamagnetic materials, which act primarily to decrease $T_2$. At low concentrations, paramagnetic materials effect $T_1$ more than $T_2$.

Paramagnetism occurs in materials that contain electrons with unpaired spins. Paramagnetic materials are characterized by a weak magnetic susceptibility (response to an applied magnetic field). Paramagnetic materials become weakly magnetic in the presence of a magnetic field and rapidly lose such activity, i.e., demagnetize, once the external field has been removed. It has long been recognized that the addition of paramagnetic materials to water causes a decrease in the $T_1$ parameter of the hydrogen nuclei.

Paramagnetic materials, for example, comprising the paramagnetic lanthanides, especially materials containing $Gd^{+3}$ have been used as magnetic resonance contrast agents primarily because of their effect on $T_1$. $Gd^{+3}$ has seven unpaired electrons in its 4f orbitals and exhibits the greatest longitudinal relaxivity of any element.

A major concern with the use of contrast agents for magnetic resonance imaging is that at magnetically effective doses many paramagnetic materials exert toxic effects on biological systems making them inappropriate for in vivo use. For example, the free solubilized form of $Gd^{+3}$ salts are quite toxic. To make the gadolinium ion more suitable for in vivo use, researchers have chelated it using diethylenetriaminepentaacetic acid (DTPA). This agent, Gd-DTPA, has been successful in enhancing magnetic resonance images of human brain and renal tumors.

Despite its satisfactory relaxivity and safety, this formulation has several disadvantages. For example, due to its low molecular weight, Gd-DTPA is cleared very rapidly from the blood stream and tissue lesions (tumors). This limits the imaging window, the number of optimally enhanced images that can be obtained after each injection, and increases the agent's required dose and its toxic effects. In addition, the biodistribution of Gd-DTPA is suboptimal for imaging body tumors and infections due to its low molecular weight.

Several approaches have been taken in attempts to overcome these disadvantages. For example, $Gd^{+3}$ and $Gd^{+3}$-chelates have been chemically conjugated to proteins such as albumin, polylysines and immunoglobulins. Drawbacks of conjugating DTPA to protein carriers for use in magnetic resonance image enhancement include inappropriate biodistribution and toxicity. In addition, proteins provided are not subject to wide synthetic variation. Additionally, thermal sterilization of protein conjugates tends to be problematic, especially in the case of albumin conjugates. Also proteins are metabolized by the body, providing an imaging agent which changes molecular weight uncontrollably. This disadvantage causes blood pool half-life tissue specificity of the imaging agent to change continuously. Proteins are immunogenic substances, which have several known drawbacks for therapeutic or diagnostic use. Solutions to these recognized problems are of importance in the areas of magnetic resonance, x-ray and fluorescence imaging.

It is apparent that it would be desirable to provide new classes of magnetic resonance contrast enhancing agents, having a specificity toward accumulation in different tissues, and which remain in the blood pool for long periods of time.

The importance of drug targeting has been recognized in recent years, especially for anticancer drugs, inasmuch as toxicity to normal cells is often dose limiting. Drug targeting has been employed in this area, using antibodies to tumor associated antigens or using other proteins and saccharides to avoid the random destruction of healthy tissue. Antibodies and portions or fragments thereof have been most widely used due to their specificity. The current approaches, however, are expensive and pose immunogenicity problems. Furthermore, not all cancers are susceptible to drug therapy.

Certain tumors are especially susceptible to treatment by radiation, such as those of hematopoietic origin, for example, leukemias and lymphomas; others are less susceptible to such treatment such as adenocarcinomas of the head and neck, or breast, ovarian, cervical or rectal adenocarcinomas. However, certain of these cancers cannot be treated by externally derived beam radiation as a practical matter because of the location of the tumor and the effect of such radiation on surrounding healthy tissue. Hence, it is advantageous to deliver a source of radiation such as a radio active isotope to the tumor, while minimizing damage to surrounding healthy tissues which in conventional treatment would likely lie in the path of the beam. It would be advantageous to deliver the appropriate radiation dosage directly to the tumor with significantly less harm to the surrounding tissue thereby increasing the therapeutic ratio (the ratio of damage to the tumor divided by damage to the most sensitive healthy tissue).

In summary, it would be advantageous to prepare a material that would overcome the following disadvantages; 1) toxicity, 2) short blood pool residence time, 3) lack of specificity for tissues which are to be targeted, 4) immunogenicity, and 5) uncontrolled metabolism of the polymer. The art records attempts at providing such a polymer.

Felder et al, U.S. Pat. No. 4,916,246 describe low molecular weight paramagnetic chelates stated to be useful for NMR imaging having the formula:

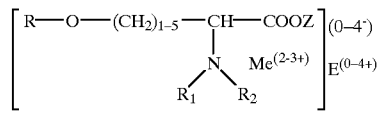

wherein Me is Fe, Mn, Dy or Gd, Z is H or a negative charge, $R_1$ and $R_2$ are substituted alkyl and R can be poly(oxy-alkyl) with 1 to 50 oxygen atoms and from 3 to 150 carbon atoms.

U.S. Pat. No. 5,137,711 describes low molecular weight complexes of paramagnetic ions with derivatives of DTPA or EDTA represented by the formula:

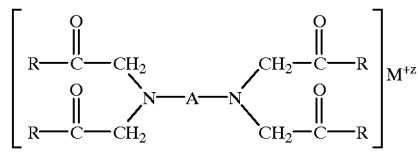

wherein A is selected from the group consisting of —CH$_2$CH$_2$— and

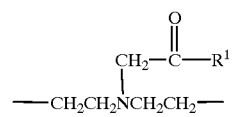

and $M^{+z}$ is a paramagnetic ion of an element with an atomic number of 21–29, 42–44 or 58–70, and a valence, Z, of +2 or +3; the $R^1$ and R groups may be the same or different and are selected from the group consisting of —O⁻ and

wherein $R^2$ is —(CH$_2$CH$_2$O)$_n$—$R^4$ wherein n is 1–10 and $R^4$ is H, alkyl having 1 to 8 carbon atoms (i.e. C$_1$–C$_8$) or aryl, unsubstituted or substituted with hydroxy, and $R^3$ is H, $R^2$, alkyl having from 1 to 8 carbon atoms, hydroxy, alkoxy having 1–8 carbon atoms, cycloalkyl with up to 10 carbon atoms or an aryl group which is optionally substituted with hydroxy, carboxy, halide, alkoxy having from 1 to 8 carbon atoms or alkyl having from 1 to 8 carbon atoms, wherein 2 of the $R^1$ groups are —O⁻ and the remainder of the $R^1$ groups are groups

Application WO 91-18630 (no English equivalents available) describes substances for treating or diagnosing tumors, having at least one aliphatic amino group, or at least one phenolic hydroxyl and/or amino group and at least one aliphatic amino group, all substituted with polyethylene glycol chains, whose degree of polymerization, n, is 5 to 250. The terminal hydroxyl group of the chain is substituted by C$_1$–C$_{12}$ alkyl ester.

Herz, et al., U.S. Pat. No. 3,859,337 describes low molecular weight ethylenediamine tetraacetic acid anhydride derivatives useful as chelating agents.

SUMMARY OF THE INVENTION

We have discovered that reactive poly(alkylene oxides) can be reacted with chelating agents or precursors thereof containing reactive functionality to form metallizable segmented polymers which, when associated with metal ions, provide higher molecular weight chelates of extraordinary utility as blood pool contrast agents for diagnostic imaging and/or as cytotoxic agents, depending upon the metal(s) incorporated in the molecule.

In one aspect, the invention provides a segmented polymeric chelate composition comprising a poly(alkylene oxidylene) moiety linked to a chelating residue, said composition having a molecular weight of at least about 4,500.

In another aspect, the invention provides a segmented polymeric chelate composition comprising a poly(alkylene oxidylene) moiety linked to a chelating residue, said composition having a molecular weight of at least about 4,500 and a metal ion associated therewith. By judicious choice of the metal ion, the invention is particularly suitable for use as a contrast agent for magnetic resonance, xray, radioscintigraphic, or fluorescence imaging or for treatment of certain diseases, especially malignancy. The composition has the structure:

Formula I

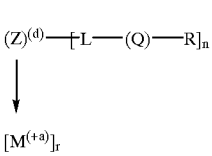

-continued $$[E^{(b)}]_w$$

wherein:

Z is a chelating residue;

Q is a divalent poly(alkylene oxidylene) moiety having a carbon terminus at R and at L;

L represents an amide linkage;

$E^{(b)}$ is one or more counterions each having a charge of b;

b is an integer from 1, 2 and 3;

n is an integer selected from the group 1, 2, 3 and 4;

w is zero or an integer from 1 to 5;

$M^{(+a)}$ is a cation, having a charge of +a;

a is an integer from 1 to 4;

r is 0 or an integer from 1 to 3, provided that when r is 2–3, each $M^{(+a)}$ can be the same or different cation;

d is the total charge on the chelating residue and is an integer from 0 to 10;

$d + \Sigma(b \cdot w) + \Sigma(a \cdot r) = 0$; and

R is a capping moiety chosen from the group consisting of hydrogen, hydroxyl, $C_1$–$C_4$ alkyl, aryl containing 6 to 24 carbon atoms, $C_2$–$C_5$ alkanoyloxyl and $C_1$–$C_4$ alkoxy, or R is an immunoreactive group or cytotoxic drug linked to Q by a chemical bond or a linking group.

The invention further provides a method of performing a diagnostic imaging procedure in a body, comprising administering to the body a contrast enhancing amount of the composition described above, and exposing at least a portion of the body to an imaging step to image at least said portion of the body.

The invention provides compositions which are particularly advantageous and effective image enhancement agents for the blood pool and remain within the vascular system for remarkably long periods of time.

This invention also provides compounds and compositions having a specificity toward accumulation in different tissues, for example, in tumors and in the liver.

Yet another advantageous feature of this invention is that the molecular weight of the above-described segmented polymers can be synthetically tailored to produce an agent of desired molecular weight, size, blood pool residence time and tissue specificity.

The invention also provides a polymer useful in chelation therapy for metal poisoning, especially heavy metal poisoning. The polymer is also useful in detecting such ions.

The invention also provides a polymer useful in detection of flows and leaks in materials that contain liquids, and in apparatus used with liquids for heating, cooling, lubrication and the like.

Still other advantageous features of this invention will become readily apparent in the following description.

DESCRIPTION OF PREFERRED EMBODIMENTS

As used herein "segmented" polymer means a polymer having one component or "segment" comprising a chelating residue Z and from one to four regions or "segments" each comprising a capped or uncapped poly(alkylene oxidylene) moiety.

As used herein the term body refers to a bounded aggregate of matter, preferably the entire material substance or organism, especially an animal, most preferably an animal or human patient.

While the segmented polymer of this invention is described herein primarily in connection with its preferred utilities, i.e., as a contrast agent for use in imaging compositions and methods, it also finds utility in other applications and fields, e.g., as a therapeutic agent, an ion scavenging agent, an ion detecting agent and the like.

The segmented polymer of this invention can have a cytotoxic agent associated therewith. By "cytotoxic agent", it is meant any agent able to kill cells, including a radionuclide, whose emissions lead to cell death. In a preferred embodiment, the cytotoxic agent is a metal ion associated with the chelating residue.

The segmented polymer of this invention can have an imaging ion associated therewith. By "imaging ion", it is meant any metal ion useful for enhancing contrast during x-ray, radioscintigraphic, fluorescence or magnetic resonance imaging. The imaging agent can be ionically associated with the chelating residue. Different types of metal ions may be employed in the same polymer so as to be useful for different types of imaging simultaneously, (for example, the ions of different elements, or different isotopes of the same element) or the same ion (e.g. ions of the same element or isotopes of the same elements) may be imaged by different methods.

The segmented polymer of the invention can comprise a therapeutic moiety and/or a moiety, preferably a metal, for enhancing contrast during imaging, and thus serve two functions simultaneously. This attribute is particularly useful in the detection and treatment of tumors.

The segmented polymer useful in the practice of the invention contains a chelating residue linked to a poly(alkylene oxidylene) moiety. Higher molecular weight polymers comprising 100 to 750 alkylene oxide units are preferred in blood pool imaging as they have longer blood pool residence times.

As used herein aryl refers to monocyclyl to hexacyclyl aryl, having from 6 to 24 carboxy atoms and may be additionally substituted with one or more $C_1$–$C_4$alkoxy, and/or $C_1$–$C_4$alkyl. Such aryls, when used in the polymer of the invention are useful for fluorescence detection.

In formula I above, Q represents a poly(alkylene oxidylene) moiety having a carbon terminus at L and a carbon terminus at R and containing m alkylene oxide units. Exemplary poly(alkylene oxidylene) moieties comprise poly(ethylene oxides), and/or poly(propylene oxides) and/or poly(butylene oxides) and the like. Preferred poly(alkylene oxidylene) moieties include poly(ethylene oxidylene) moieties (PEO), polypropylene oxidylene) (PPO) and random and block copolymers of PEO and PPO. PEO containing polymers are particularly preferred when it is desired for the final polymer to possess solubility in water. It is also contemplated that the poly(alkylene oxidylene) moiety can comprise glycerol poly(alkylene oxide) triethers, polyglycidols, linear, block and graft copolymers of alkylene oxides with compatible comonomers such as poly(ethyleneimine-co-ethylene oxide), or poly(oxazoline-co-alkyleneoxide) and grafted block copolymers such as poly(methyl vinyl ether-co-ethylene oxide). For magnetic resonance imaging applications, preferred polymers of this invention have an average molecular weight (MW) greater than 4,500, more preferably 4,500–40,000 MW. These polymers can be derived from poly(alkylene oxidylene) moieties which are commercially available in the corresponding alcohol form as a diol, or as a monoalkyl ether alcohol, or monoalkyl ether monoamine form, or alternatively they can be prepared by techniques well known to those skilled in the art. The number of alkylene oxide subunits in Q depends upon 1) n, the number of L—Q—R segments extending from Z; 2) upon the "molecular" weight of each alkylene oxide subunit moiety; 3) the desired molecular weight of the polymer; 4) the molecular weight of R and Z, as well as $M^{+a}$. If n is greater than 1, each poly(alkylene oxide) moiety may be the same or different. Expressed mathematically this is: n×[(MW of L & R)+(MW of alkylene oxide subunit×m)]+(r×atomic weight of chelated metal(s))+MW of chelating residue+molecular weight of Z=MW of the polymer. Thus m is a function of n for a given molecular weight of the polymer. A particularly preferred class of poly(alkylene oxide) moieties derived from poly(ethylene oxides) can be represented by the structure:

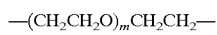

If four PEO chains are present (n=4) then upper limit of the most preferred molecular weight of 40,000 will be obtained with m=about 220. If a molecular weight of 5,000 is desired in the same type of polymer (n=4) then m will be closer to 30.

These poly(alkylene oxide) moieties and their reactive derivatives, useful in preparing the segmented polymer of the invention, are known in the art. For example, bis(methyl amino) polyethylene glycol and its use as an intermediate is known in the art, for example; Mutter, *Tetrahedron Letters*, 31, 2839–2842 (1978) describes a procedure to convert the terminal hydroxyl groups of poly(ethylene oxide) to reactive primary amino groups as well as the preparation of a number of reagents bound to poly(ethylene oxide) amines; Harris et al., *J. Polymer. Science*, 22, 341–352 (1984) describe various PAG derivatives including for example, amino poly (ethylene oxide). Other poly(alkylene oxide) derivatives are prepared by known chemistries, examples of which are described hereinbelow.

As is well known, a chelating molecule is a compound containing electron donor atoms that can combine by coordinate bonding with a cation to form a coordination complex or chelate. This class of compounds is described in the *Kirk-Othmer Encyclopedia of Chemical Technology*, Vol. 5, 339–368. By analogy, in the segmented polymer of the invention the chelating residue is a chelating moiety which is a radical or a multivalent radical, rather than a molecule or a compound in itself. The polymer incorporating the chelating residue could thus be described as a chelating polymer.

In structure I above, Z represents a chelating residue. The chelating residue can be derived and/or selected from moieties which contain electron donor atoms. These moieties can be selected from, for example, polyphosphates, such as sodium tripolyphosphate and hexametaphosphoric acid;

aminocarboxylic acids, such as ethylenediaminetetraacetic acid, N-(2-hydroxyethyl)ethylenediaminetriacetic acid, nitrilotriacetic acid, N,N-di(2-hydroxyethyl) glycine, ethylenebis(hydroxyphenylglycine) and diethylenetriamine pentaacetic acid;

1,3-diketones, such as acetylacetone, trifluoroacetylacetone, and thienoyltrifluoroacetone; and hydroxycarboxylic acids, such as tartaric acid, mucic acid, citric acid, gluconic acid, and 5-sulfosalicylic acid;

polyamines, such as ethylenediamine, diethylenetriamine, triethylenetetramine, and triaminotriethylamine;

aminoalcohols, such as triethanolamine and N-(2-hydroxyethyl)ethylenediamine;

aromatic heterocyclic bases, such as 2,2'-dipyridyl, 2,2'-diimidazole, dipicoline amine and 1,10-phenanthroline;

phenols, such as salicylaldehyde, disulfopyrocatechol, and chromotropic acid;

aminophenols, such as 8-hydroxyquinoline and oxine-sulfonic acid;

oximes, such as dimethylglyoxime and salicylaldoxime;

peptides containing proximal chelating functionality such as polycysteine, polyhistidine, polyaspartic acid, polyglutamic acid, or combinations of such amino acids, each polyamino acid containing from 2 to about 20 amino acids in the polymer;

Schiff bases, such as disalicylaldehyde 1,2-propylenediimine;

tetrapyrroles, such as tetraphenylporphin and phthalocyanine;

sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea;

synthetic macrocylic compounds, such as dibenzo[18] crown-6, $(CH_3)_6$-[14]-4,11-diene-$N_4$, and (2.2.2)-cryptate; and phosphonic acids, such as nitrilotrimethylenephosphonic acid, ethylenediaminetetra(methylenephosphonic acid), and hydroxyethylidenediphosphonic acid, or combinations of two or more of the above agents.

Preferred chelating residues contain one or more carboxylic acid or carboxylate groups and include elements present in: ethylenediamine-N,N,N',N'-tetraacetic acid (EDTA); N,N,N',N'',N''-diethylenetriaminepentaacetic acid (DTPA); 1,4,7,10-tetraazacyclododecane-N,N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans(1,2)-cyclohexanodiethylenetriamine pentaacetic acid (CDTPA);

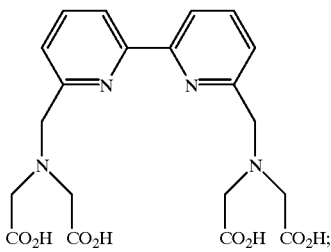

(B4A)

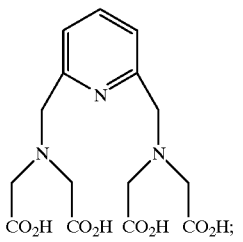

(P4A)

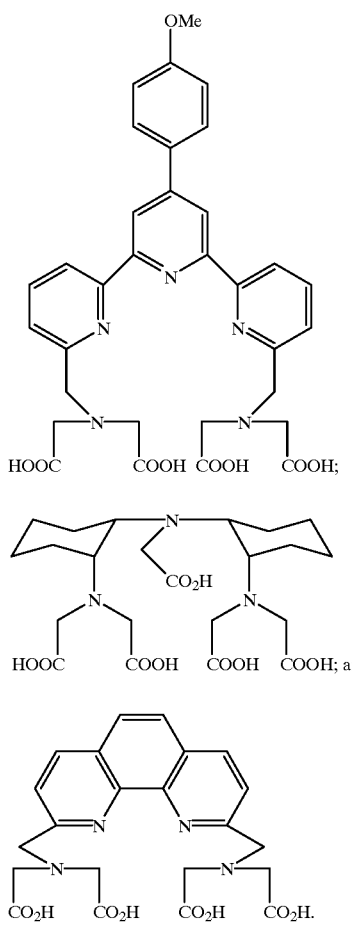

(TMT)

(DCDTPA)

(PheMT)

Such chelating compounds, including their preparation and chemical manipulation are known in the art. For example, the acid and anhydride forms of EDTA and DTPA are commercially available. Methods for preparing B4A, P4A and TMT are described in U.S. Pat. No. 4,859,777; the disclosure of which is hereby incorporated by reference. Other suitable chelating groups are known in the art, and are described in PCT/US91/08253, and many other readily available references.

If Z is a chelating residue made of multiple chelating moieties or subunits, each of the subunits can be linked together by a linking group. Thus, more than one chelating moiety can be used to make up the chelating residue. If more than one chelating moiety is present in the chelating residue, these may be the same or different. Chelating moieties can be linked together using known chemistries and materials. Thus the chelating residue can be one moiety or a "core" of chelating moieties. For example, a core of DTPA residues may be prepared by reacting DTPA dianhydride with a diamine, such as ethylene diamine, to form a "core" of DTPA chelators. The anhydrides react with the amine to form amide bonds. Two DTPA moieties linked by one ethylene diamine and three DTPA moieties linked by 2 ethylene diamines are examples of preferred "cores" containing multiple DTPA residues, others are contemplated. Other chelating residues, made up of multiple chelating moieties are well known in the art and are prepared by known chemistries as well.

It is contemplated that the polymer may be prepared so as to form a polymer useful in imaging diseased tissue or state, i.e. useful in identifying or diagnosing the diseased area, and also useful in treating the area optionally in the same dose. This is accomplished by judicious choice of R which can be cytotoxic, or useful in imaging (e.g. fluorescence imaging if aryl) and of M, the chelated metal, which can be a cytotoxic radionuclide or an imaging agent in radioscintigraphy, x-ray, fluorescence or MR imaging.

For magnetic resonance imaging applications, $M^{(+a)}$ represents a paramagnetic metal ion such as an ion of atomic number 21 to 29, 42, 44 and 58 to 70. Ions of the following metals are preferred: Cr, V, Mn, Fe, Co, Ni, Cu, Ce, Pr, Nd, Pm, Sm, Eu, Gd, Tb, Dy, Ho, Er, Tm and Yb. Especially preferred are $Cr^{+3}$, $Cr^{+2}$, $V^{+2}$, $Mn^{+3}$, $Mn^{+2}$, $Fe^{+3}$, $Fe^{+2}$, $Co^{+2}$, $Gd^{+3}$ and $Dy^{+3}$. $Gd^{+3}$ and $Dy^{+3}$ are most preferred.

For fluorescent imaging applications $M^{+a}$ represents a fluorescent metal ion preferably a metal of atomic number 57 to 71, most preferably a $Eu^{+3}$ ion.

$M^{(+a)}$ can be a radioactive metal ion isotope. As such, it can be a cytotoxic agent and/or an agent useful in diagnostic imaging such as in radioscintigraphy.

By "cytotoxic agent", it is meant any agent able to kill cells, including, in addition to a chelate of a radionuclide that omits cytotoxic radiation, chemotherapeutic agents such as cytotoxic drugs and cytotoxic antibiotics, toxins or any agent which initiates or which leads to cell death.

The radioactive metal isotope can be an ion of an isotope of a metal selected, for example, from Sc, Fe, Pb, Ga, Y, Bi, Mn, Cu, Cr, Zn, Ge, Mo, Tc, Ru, In, Sn, Re, Sr, Sm, Lu, Dy, Sb, W, Re, Po, Ta and Tl ions. Preferred isotopes of radioactive metal ions include $^{44}Sc$, $^{64,67}Cu$, $^{111}In$, $^{212}Pb$, $^{68}Ga$, $^{90}Y$, $^{153}Sm$, $^{212}Bi$, $^{99}mTc$ and $^{186,188}Re$ for therapeutic and diagnostic imaging applications.

Specifically contemplated are segmented polymers where r (the number of metals in the chelating residue) is greater than 1, and in those cases each $M^{+a}$ can represent the same or a different cation in the polymer; for example a polymer having $[Mn^{+2}]2[Gd^{+3}]$ is specifically contemplated; as is $[Gd^{+3}]2[^{67}Cu^{+2}]2$ or any other combinations within or between the classes of cations used in the polymer. Such polymers are thus useful for more than one type of imaging or cytotoxic therapy. It is understood that the sum of positive charges ($\Sigma r \cdot a$) is the sum of net positive charge for all cations. Thus for the listed examples above, $\Sigma(r \cdot a)$ is 7 and 10, respectively. For example, if Z, the chelator moiety, has 5 free carboxylates, (d=−5) and one $Gd^{+3}$ chelated therein ($M^{+a}=Gd^{+3}$; a=+3), then the total charges of counter ion (w×b) must be +2, thus if w is 1 b is +2 as in calcium or magnesium; if w is 2 b is +1 as in a proton (assumed ionic for our purposes in formula I), sodium or potassium. If Z; has d=−3 and chelates Gd+3 )a=+3), no counter ion is required, but they may exist if E(w×b)=O.

When E is present, i.e., when w is not zero, b most preferably is 1 or 2. E is preferably a pharmaceutically acceptable cation or anion. The skilled artisan, armed with this disclosure and the prior art will be able to choose such counterions for their best benefit. The total positive charge on the cations $\Sigma(r \cdot a)$ equals the sum of the total charge on the chelating residue group (d), plus the total charge on any counterions E present (b). When r=0, then w=0. When r=1, w can be 0, 1, 2, 3, 4 or 5. In the most preferred embodiment r is 1 and w is 0, a=d+b.

E in formula I can be one or more counterions. For example, E can be one or more anions, such as a halide; sulfate; phosphate; nitrate; and acetate and the like. E can be one or more cations such as $Na^+$, $K^+$, meglumine, and the like. For in vivo applications, particularly for diagnostic imaging applications, nontoxic physiologically tolerable anions and cations are, of course, desirable.

Where r is 0 the segmented polymers of the invention can be used in chelation therapy to treat heavy metal poisoning, e.g. lead poisoning and the like. For treatment of heavy metal poisoning, the polymers are administered alone without chelated ions, or in some applications of metal poisoning treatment, some other metal ions such as calcium are chelated by the polymer prior to administration. It is contemplated that such polymers as non chelated materials, as completely chelated or as mixtures of non chelated and chelated polymers can be used to treat poisoning from such metal ions as Sc, Ti, V, Cr, Mn, Fe, Eu, Er, Pb, Co, Ni, Cu, Ga, Sr, Y, Zr, U, Pu, Tc, Ru, In, Hf, W, Re, Os, Dy, Gd, Hf, La, Yb, Tc, As and the like.

In a mixture of chelated and non chelated polymers of this invention, wherein a metal is associated with the chelating residue in some of the segmented polymers of the mixture, the metal content in the mixture can vary from about 0.1 up to about 12% based on the total weight of the polymer in the mixture. Preferably, the mixture of segmented polymers preferably contains the metal in an amount of from 1% to 5%, more preferably 1–4% by weight. Such mixtures can be formed by treating unchelated polymer with enough metal ion to chelate to from 1% to 15% or preferably from 1% to 10% by weight of the mixture.

The composition of this invention can be capped at the termini with groups represented by R in formula I linked to the termini of the poly(alkylene oxide) alkylene groups by a chemical bond or a linking group. These can be independently selected from hydrogen, hydroxy, $C_1$–$C_4$alkyl, aryl as defined above, carboxy, $C_2$–$C_3$alkanoyloxy, and $C_1$–$C_4$alkoxy. In preferred embodiments, the polymer can be capped by reagents that produce acyl derivatives, for example, by monoanhydrides, e.g., acetic anhydride or succinic anhydride and iodoacetic acid anhydride which forms an iodomethyl carbonyloxy intermediate that can be further reacted with an R precursor such as a protein or cytotoxic agent.

R in formula I can also be a cytotoxic drug, for example, a cytotoxic drug useful in the treatment of cancer. The cytotoxic drug will be selected with reference to factors such as, for example, the type of cancer tumor and the efficacy of a certain chemotherapy agent for treating the cancer tumor involved. The chemotherapy agent may be selected from alkylating agents, antimetabolites, natural products useful as cytotoxic drugs, hormones and antagonists and other types of cytotoxic compounds.

Examples of alkylating agents include the nitrogen mustards (i.e. the 2-chloroethylamines) such as, for example, chloromethine, chlorambucil, melphalan, uramustine, mannomustine, extramustine phosphate, mechlorthaminoxide, cyclophosphamide, ifosamide and trifosfamide; alkylating agents having a substituted aziridine group such as, for example, tretamine, thiotepa, triaziquone and mitomycin; alkylating agents of the alkyl sulfonate type, such as, for example, busulfan, hepsulfam, and piposulfan; alkylating N-alkyl-N-nitrosourea derivatives such as, for example, carmustine, lomustine, semustine or streptozotocine; alkylating agents of the mitobronitole, dacarbazine and procarbazine type; and platinum complexes such as, for example, cisplatin and carboplatin and others.

Examples of antimetabolites include folic acid derivatives such as, for example, methotrexate, aminopterin and 3'-dichloromethotrexate; pyrimidine derivatives such as, for example, 5-fluorouracil, floxuridine, tegafur, cytarabine, idoxuridine, and flucytosine; purine derivatives such as, for example, mercaptopurine, thioguanine, azathioprine, tiamiprine, vidarabine, pentostatin and puromycin and others.

Examples of natural products useful as cytotoxic agents include for example vinca alkaloids, such as vinblastine and vincristine; epipodophylotoxins such as, for example, etoposide, and teniposide; antibiotics such as, for example, adrimycin, daunomycin, dactinomycin, daunorubicin, doxorubicin, mithramycin, bleomycin and mitomycin; enzymes such as, for example, L-asparaginase; biological response modifiers such as, for example, alpha-interferon; camptothecin; taxol; and retinoids such as retinoic acid and the like.

Examples of hormones and antagonists include adrenocorticoids, such as, for example, prednisone; progestins, such as, for example, hydroxyprogesterone acetate, medroxyprogesterone acetate and megestrol acetate; estrogens such as, for example, diethylstilbestrol and ethinyl estradiol; antiestrogens such as for example, tamoxifen; androgens such as, for example, testosterone propionate and fluoxymestrone; antiandrogens such as, for example, flutamide; and gonadotropin-releasing hormone analogs such as, for example, leuprolide.

Examples of miscellaneous agents include anthracenediones such as for example, mitoxantrone; substituted ureas such as, for example, hydroxyureas; and adrenocortical suppressants such as, for example, mitotane and aminoglutethimide.

In some embodiments, R is an immunoreactive group covalently bonded to Q through a linking group. As used herein, the term "immunoreactive group" is meant to include an organic compound which is capable of being covalently bound to the polymer and which is found in a living organism or is useful in the diagnosis, treatment or genetic engineering of cellular material or living organisms, and which has a capacity for interaction with another component which may be found in biological fluids or which may be associated with cells to be treated such as tumor cells.

The concept of drug targeting has gained importance in recent years, especially for anticancer drugs, inasmuch as toxic side effects of anticancer drugs to normal cells are a primary obstacle in cancer chemotherapy due to lack of selectivity to cancer cells. However, the desirability of targeting a certain tissue type finds application in other areas as well. Drug targeting can be accomplished by conjugation of the drug with, or encapsulation in, a specific transporter to the target. Immunoreactive groups or materials such as proteins, saccharides, lipids and synthetic polymers have been used for such transporters. Antibodies have been most widely used of these perhaps due to their target specificity and wide applicability.

Depending upon the intended use, the immunoreactive group can be selected from a wide variety of naturally occurring or synthetically prepared materials, including, but not limited to enzymes, amino acids, peptides, polypeptides, proteins, lipoproteins, glycoproteins, hormones, drugs (for example digoxin, phenytoin, phenobarbitol, thyrozine, triiodothyronine, gentamicin, carbamazepine, and theophylline), steroids, vitamins, polysaccharides, viruses, protozoa, fungi, parasites, rickettsia, molds, and components thereof, blood components, tissue and organ components, pharmaceuticals, haptens, lectins, toxins, nucleic acids (including oligonucleotides), antibodies, antigenic materials (including proteins and carbohydrates), avidin and derivatives thereof, biotin and derivatives thereof, histones and others known to one skilled in the art.

Preferred immunoreactive groups (sometimes referred to in the art as ligands) are those which have a receptor molecule specific to the ligand of interest. Thus, a specific binding reaction involving ligand, R, and receptor to form a ligand-receptor complex can be used for targeting, and treatment, and for imaging a target site. Examples of such ligand-receptor complexes include, but are not limited to antibody-antigen, avidin-biotin, histone-DNA, repressor (inducer), promoter of operons and sugar-lectin complexes. Additionally, complementary nucleic acids, both natural and antisense are also considered specific binding materials as the term is used herein. Either component of the above listed pairs can be useful as a ligand if the other component is found or attached to the target site.

Useful immunoreactive groups include (1) any substance which, when presented to an immunocompetent host, will result in the production of a specific antibody capable of binding with that substance, or (2) the antibody so produced, which participates in an antigen-antibody reaction. Thus, the immunoreactive group can be an antigenic material, an antibody, or an anti-antibody. Both monoclonal and polyclonal antibodies are useful. The antibodies can be whole molecules or various fragments thereof, as long as they contain at least one reactive site for reaction with the reactive groups on the complexing agent or with linking groups as described herein.

In certain embodiments, the immunoreactive group can be an enzyme which has a reactive group for attachment to a complexing agent. Representative enzymes include, but are not limited to, aspartate aminotransaminase, alanine aminotransaminase, lactate dehydrogenase, creatine phosphokinase, gamma glutamyl transferase, alkaline acid phosphatase, prostatic acid phosphatase, tissue plasminogen activator, horseradish peroxidase and various esterases.

If desired, the immunoreactive group can be modified or chemically altered to provide reactive groups for linking the immunoreactive group to the polymer. These methods are well known in the art. Such techniques include the art recognized use of linking moieties and chemical modification such as described in WO-A-89/02931 and WO-A-89/2932, which are directed to modification of oligonucleotides, and the disclosure of U.S. Pat. No. 4,719,182, which is incorporated herein by reference. Where the reactive group for linking the immunoreactive group to the polymer is attached to a protein, antibody and the like, it is called a "protein reactive group".

Two highly preferred uses for the compositions of this invention where R is an immunoreactive group are for the diagnostic imaging of tumors and the radiological treatment of tumors. Preferred immunoreactive groups therefore include antibodies, or immunoreactive fragments thereof, to tumor-associated antigens. Specific examples include B72.3 antibodies (described in U.S. Pat. Nos. 4,522,918 and 4,612,282) which recognize colorectal tumors, 9.2.27 antimelanoma antibodies, D612 antibodies which recognize colorectal tumors, UJ13A antibodies which recognize small cell lung carcinomas, NRLU-10 antibodies which recognize small cell lung carcinomas and colorectal tumors (Pancarcinoma), 7E11C5 antibodies which recognize prostate tumors, CC49 antibodies which recognize colorectal tumors, TNT antibodies which recognize necrotic tissue, PR1A3 antibodies, which recognize colon carcinoma, ING-1 antibodies, which are described in International Patent Publication WO-A-90/02569, B174 antibodies which recognize squamous cell carcinomas, B43 antibodies which are reactive with certain lymphomas and leukemias and others which may be of particular interest.

Such antibodies and other useful immunological groups described above are large, complex protein molecules having multiple sites for appendage of the segmented polymer complexing agent. Consequently, the immunoreactive group can have appended to it additional complexing agents each via one of the protein reactive groups. Thus, the term immunoreactive group is intended to include immunological groups having at least one segmented polymer molecule bonded thereto through at least one protein reactive group.

Additionally, the immunoreactive group can be an antibody or fragment thereof containing a carbohydrate region which can be attached to the polymer through the carbohydrate region such as described in U.S. Pat. No. 4,937,183. Useful methods for attaching an antibody are also described in U.S. Pat. Nos. 4,671,958; 4,699,784; 4,741,900; and 4,867,973.

Additionally, immunoreactive groups that interact with intracellular components are also specifically contemplated; for example, actin, myosin, histone, DNA, DNAase and the like. These molecules, while useful in all contemplated applications, are preferred for targeting solid tumors and necrotic cells. Specifically contemplated in this embodiment is the use of a histone linked to the polymer of the invention for imaging solid tumors. Histones have low immunogenicity, bind tightly to nucleic acids, and have difficulty passing through cell and nuclear membranes in intact living cells. However, in necrotic tissue, the cell and nuclear membranes no longer function and are often perforate, allowing entry of foreign materials, including histones. This diffusion into necrotic tissue can be used to accumulate an imaging and/or cytotoxic agent of this invention in the vicinity of cancer cells, especially in solid tumors. Necrosis can occur naturally due to a limited blood supply, or can be induced by cytotoxic agents or irradiation. Thus, this method is useful in imaging and/or treatment of tumors. As a further example, DNAase when attached to the polymer of the invention can be used to target for detection and destruction, free DNA.

Free DNA accumulates in certain diseases, such as systemic lupus where it ultimately causes kidney failure. Thus this polymer can be used to detect DNA accumulation in kidney glomeruli and destroy it as well.

The immunoreactive group can be attached to the polymer by methods known in the art for derivatizing any functional groups typically found on proteins, or other immunoreactive groups. However, it is specifically contemplated that the immunoreactive group can be a nonprotein biomolecule. Thus, a linking group precursor useful in preparing the polymer of the invention will include those groups which can react with any biological molecule containing an immunoreactive group, whether or not the biological molecule is a protein, to form a linking group between the polymer agent and the immunoreactive group.

Preferred linking group precursors can be selected from but are not limited to:

(1) A group that will react directly with the amine or sulfhydryl groups on the protein or biological molecule containing the immunoreactive group, for example, active halogen containing groups including, for example, chloromethylphenyl groups and chloroacetyl [Cl—$CH_2$CO—] groups, activated 2-leaving group substituted ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like; and other groups known to be useful in conventional photographic gelatin hardening agents.

(2) A group that can react readily with modified proteins or biological molecules containing the immunoreactive group, i.e., proteins or biological molecules containing the immunoreactive group modified to contain reactive groups such as those mentioned in (1) above, for example, by oxidation of the protein to an aldehyde or a carboxylic acid, in which case the "protein reactive group" can be selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 18 carbon atoms. The aryl portions of the protein reactive group can contain from about 6 to about 20 carbon atoms.

(3) A group that can be linked to the protein or biological molecule containing the immunoreactive group, or to the modified protein as noted in (1) and (2) above by use of a crosslinking agent. Certain useful crosslinking agents, such as, for example, difunctional gelatin hardeners, bisepoxides and bisisocyanates become a part of, i.e., a linking group in, the protein-segmented polymer complexing agent conjugate during the crosslinking reaction. Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847 and the dication ethers of U.S. Pat. No. 4,877,724. With these crosslinking agents, one of the reactants must have a carboxyl group and the other an amine, alcohol, or sulfhydryl group. The crosslinking agent first reacts selectively with the carboxyl group, then is split out during reaction of the "activated" carboxyl group with, for example, an amine to form an amide linkage between the protein or cytotoxic agent and the segmented polymeric chelating agent, thus covalently bonding the two moieties. An advantage of this approach is that crosslinking of like molecules, e.g., proteins with proteins or complexing agents with complexing agents, is substantially avoided where the agent has one reaction site, whereas the reaction of difunctional crosslinking agents is less selective and unwanted crosslinked molecules can be obtained. Especially preferred protein reactive groups include amino and isothiocyanato.

The composition of this invention can be prepared in water-soluble or water dispersable forms depending upon the intended application. Such compositions have a molecular weight of at least 4,500, preferably 4,500 to 40,000.

The composition of this invention can be prepared by reacting a reactive poly(alkylene oxidyl) species, such as a poly(alkylene oxidyl)amine with a chelating agent containing reactive functionality (such as an anhydride, for example) in a non-reactive solvent to form an amide bond in the composition. The poly(alkylene oxide) can be capped as described above or uncapped.

The preferred reaction conditions, e.g., temperature, pressure, solvent, etc., depend primarily on the particular reactants selected and can be readily determined by one skilled in the art.

Suitable reactive poly(alkylene oxidyl) species useful in the preparation and linking to R groups as described above include terminally functionalized poly(alkylene oxidyl) amines, poly(alkylene oxidyl) hydrazines, poly(alkylene oxidyl) isocyanates, poly(alkylene oxidyl) aldehydes, poly (alkylene oxidyl) carboxylic acids, poly(alkylene oxidyl) vinyl sulfonyl ethers, poly(alkylene oxidyl) phosphates, poly(alkylene oxidyl) N-alkylaminophosphoramidates, poly (alkylene oxidyl) epoxides, poly(alkylene oxidyl) alkoxides, poly(alkylene oxidyl) sulfonates, poly(alkylene oxidyl) halides, and the like. The above-described poly(alkylene oxidyl) species are linear and functional at both termini or at one terminus and end capped at the other terminus, for example with an ether group or a protecting group such as an acyl group or such as a trityl or dimethoxy trityl group and other protecting groups used in peptide synthesis. These protecting groups can be removed to permit reactions to produce amine or carboxyl moieties. These species are prepared by simple chemical transformations which are conventional and well known to those skilled in the art of chemistry used for effecting changes in functional groups in known compounds when preparing polymers, in this case the polymers of the invention. For example, acylation of hydroxy- or amino-substituted species to prepare the corresponding esters or amides, respectively; simple aromatic and heterocyclic substitutions or displacements; cleavage of alkyl or benzyl ethers to produce the corresponding alcohols or phenols; and hydrolysis of esters or amides to produce the corresponding acids, alcohols or amines, preparation of anhydrides, acid halides, aldehydes, simple aromatic nitration and reduction to amine and conversion to isothiocynate with thiophosgene, and the like as desired can be carried out.

Such transformations will also provide suitable chelating agents, reactive functional groups or chelating agents (and precursors thereof) containing reactive functionality when applied to functional groups in chelating agents listed above, including for example, polycarboxylic acids in anhydride form, sulfonyl chlorides, alkyl sulfates, vinyl sulfones, N-hydroxysuccinimide and other reactive esters, and the like. Sulfonyl chlorides, alkyl sulfates, vinyl sulfones and the like can be reacted with diamines such as ethylene diamine in excess to form multiple chelating agent cores as described above, or, if desired, single chelating agents linked for example by sulfonamidoethylene alkyleneamineethylene, sulfonatoethylene and the like groups respectively, to amino groups. Similarly, amino acids such as glycine or carboxy protected amino acids such as methylesters will react at the amine sites of the amino acids with the above functional groups to provide chelating agents that contain carboxylic acid groups liked to the chelator in the analogous fashion. These carboxylicacid groups can then be activated for reaction with amine containing poly (alkylene oxide) groups to form amide bonds. The amine containing chelators can react with carboxylic acid containing poly(alkylene oxide) groups or with active esters or anhydrides and the like thereof to form amide groups. Preferably there will be at least m reactive functional groups on the chelator so that m poly(alkylene oxidyl) amide bonds can be formed. Variations in the functional group type, for example, using a vinyl sulfone and then an activated hydroxysuccinimide or an anhydride plus a more reactive acyl-N-methyl imidazolium salt will permit sequential substitution of the chelator moiety by poly(alkylene oxidyl) amines having different molecular weights from each other. Alternatively, a chelator containing multiple functional groups such as anhydrides can be treated in sequence with less than stoichiometric amounts of different amine containing poly(alkylene oxidyl) moieties to provide amide link segmented polymers.

As will be recognized by one skilled in the art, obtaining the desired product by some reactions will be better facilitated by blocking or rendering certain functional groups inert. This practice is well recognized in the art, see for example, Theodora Greene, *Protective Groups in Organic Synthesis* (1991). Thus when reaction conditions are such that they may cause undesired reactions with other parts of the molecule, for example, in portions of the chelator intended to become ligands, the skilled artisan will appreciate the need to protect these reactive regions of the molecule and will act accordingly. The chelating residue containing reactive functionality can be prevented from reacting to form undesired products by suitably blocking the chelating residue precursor which can be contacted with the reactive poly(alkylene oxide) moiety to form the polymer, and then the blocking group can be subsequently removed by techniques known in the art. For example, if hydroxy substituents are to be selectively present in the final polymer, they preferably should be temporarily blocked during the segmented formation polymer, such as formation of an alkyl or trityl ether from the hydroxyl by conventional blocking techniques to minimize formation of undesirable by products and then deblocking with, for example $BBR_3$ or $CF_3COOH$, respectively, after formation of the segmented polymer. However, by products which contain one or more linkages formed by unblocked reactive precursor groups in the backbone of the polymer are contemplated to be useful.

Suitable amine functionalized reactive poly(alkylene oxide) species can be prepared by methods known in the art. For example, a preferred poly(alkylene oxide)amine can be prepared by reacting an activated form of the poly(alkylene oxide) such as halide or sulfonate ester with ammonia, a primary amine, an amide or an azide followed by reduction. Alternatively, the amino group can be introduced by other methods known in the art. (Cf. Leonard et al, *Tetrahedron* 40 1581–1584 (1984); David et al., U.S. Pat. No. 4,179,337; Gerhandt et al., *Polym. Bull* 18 487–93 (1987)). Suitable illustrative amines include N-methylamine, amino acids such as glycine and the like, aminomethyl pyridine, aminomethylthiophene, methoxyethoxyethylamine, methoxyethylamine and aminobenzoic acid. Poly(alkylene oxide) amines are commercially available, known in the art, or can be prepared by known methods, including those described herein.

The activated form of the poly(alkylene oxide) is reacted preferably with a stoichiometric excess of an amine, in an inert solvent preferably at a temperature (e.g., 100–160° C.) and pressure (e.g., 1 to 10 atmospheres) sufficient to drive the reaction to completion. Suitable inert solvents include dioxane, DMF, ethanol, or other alcohols and the like. Thereafter, the poly(alkylene oxide) amine preferably is isolated, e.g., by evaporation or precipitation, and purified, e.g., by dissolving in a suitable solvent such as methylene chloride, chloroform or trichloroethane, and then washed with an excess of aqueous NaOH, or by any other suitable isolation and purification techniques available to the skilled artisan.

Suitable carboxyl functionalized reactive poly(alkylene oxide) species can be prepared by methods known in the art. For example, a preferred poly(alkylene oxidyl) carboxylic can be prepared by reacting a hydroxyl containing poly(alkylene oxide) with a cyclic anhydride or with chloro- or bromo- or iodoalkyl acids such as chloroacetic acid and the like using potassium carbonate as a base. The terminal hydroxy group can also be oxidized to a carboxylic acid group. Alternatively, the amine containing poly(alkylene oxides) above can be elaborated by similar chemistry into carboxylic acid containing poly(alkylene oxides). Additionally, reaction of a haloalkyl poly(alkylene oxide) or with a poly(alkylene oxide) sulfonate ester with an amino acid as above provides a carboxylic acid containing poly(alkylene oxide). These materials can be purified and isolated using techniques outlined above. These carboxylic acid containing poly(alkylene oxides) or activated derivatives thereof can react with amine containing chelating agents to form amide groups in the preparation of the segmented polymers of this invention.

Materials for preparing the prefered embodiment, such as the internal anhydride forms of the chelating agents described above, are commercially available and/or can be prepared by techniques known in the art. For example, the internal anhydride form DTPA is commercially available. The internal anhydride forms of B4A, P4A and TMT can be prepared by techniques known in the art. For example, the anhydrides can be prepared by heating the corresponding acids in acetic anhydride in the presence of pyridine as catalyst. Mixed anhydrides of chelators are also suitable for segmented polymer formation.

In a preferred embodiment the reactive poly(alkylene oxide) amine can be reacted with the internal dianhydride in a suitable solvent to form the unmetallized composition. The reaction conveniently can take place at approximately room temperature and atmospheric pressure. However, higher and lower temperatures and pressures are contemplated. Suitable solvents include dimethylsulfoxide, dimethylformamide, acetonitrile, chloroform, dichloromethane, 1,2-dichloroethane and other aprotic solvents. The nonmetallized polymer preferably is isolated and then purified, e.g., by diafiltration or other methods available to the skilled artisan. Reaction without solvent in molten polyalkylene oxide is contemplated.

Alternatively, the segmented polymer can be prepared in a condensation polymerization reaction between a suitable poly(alkylene oxidyl) amine and a metallized chelating group containing carboxylic acid functionality not participating in the chelators, in a suitably activated form.

In the preferred embodiment, the metallized polymer can be formed by contacting the unmetallized polymer sequentially or simultaneously with one or more sources of metal ions. This can be conveniently accomplished by adding one or more metal ion solutions or one or more metal ion solid salts or metal ion oxides, preferably sequentially, to a solution, preferably an aqueous solution, of the polymer. Thereafter, or between sequential addition of metal ions, the chelated polymer preferably is diafiltered in water to remove excess unbound metal or can be isolated by other methods known in the art.

The composition preferably is prepared in a water soluble form, more preferably in an injectable form for diagnostic imaging or as a composition intended to be administered intravenously. The preparation of water-soluble compositions of at least 4,500 in molecular weight can be accomplished by conventional means by one skilled in the art.

It is known in the art that the size and charge of the polymer, as well as potential interactions with blood components, can influence the biodistribution of the polymer. Thus, judicious polymer synthesis can result in passive tissue targeting by the polymer.

The skilled artisan will recognize that inflammation of tissues will perturb the normal physiology of that tissue and thus perturb the half life and concentration of macromolecules (such as proteins or the polymer of the invention) in the inflamed tissue or inflamed tissue site. Thus the polymer finds utility in imaging and/or treating such inflamed tissues or inflamed tissue sites.

The skilled artisan will also appreciate that the absence of a lymphatic system in a tissue will perturb the concentration and increase the half life of macromolecules in a tissue because no convenient mechanism (e.g. the lymphatic system) is provided for the scavenging of such macromolecules. Such is the case in growing tumors. One can deliver the polymer as a cytotoxic agent, and/or an imaging agent to the growing tumor surface based on size of the polymer and on vasculature of the surrounding or targeted tissue. Thus, dosing with the appropriate molecular weight polymer will result in accumulation of such polymer in the growing surface of the tumor.

Actual dosage levels of active ingredient in the compositions of the present invention may be varied so as to obtain an amount of active ingredient that is effective to obtain a desired therapeutic or diagnostic response. The selected dosage level therefore depends upon the desired therapeutic or diagnostic effect, on the route of administration, on the desired duration of treatment and other factors.

The total daily dose of the compounds of this invention administered to a host in single or divided dose may be in amounts, for example, of from about 1 picomole to about 10 millimoles of cytotoxic agent per kilogram of body weight. Dosage unit compositions may contain such amounts or such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The dosages of the contrast agent used according to the method of the present invention will vary according to the precise nature of the contrast agent used. Preferably however, the dosage should be kept as low as is consistent with achieving contrast enhanced imaging and volumes minimized for IV drip or bolus injection. In this way, the toxicity potential is minimized. For most magnetic resonance contrast agents the current appropriate dosage will generally range from 0.02 to 3 mmol paramagnetic metal/kg body weight, especially 0.05 to 1.5 mmol/kg, particularly 0.08 to 0.5, more-especially 0.1 to 0.4 mmol/kg. However, it is anticipated that the amount of contrast agent needed will decrease as detection sensitivity in imaging machines increases. It is well within the skill of the average practitioner in this field to determine the optimum dosage for any particular magnetic resonance contrast agent by relatively routine experimentation, for both in vivo or in vitro applications.

Contrast agents may be formulated with conventional pharmaceutical or veterinary aids, for example stabilizers, antioxidants, osmolality adjusting agents, buffers, pH adjusting agents, and the like, and may be in a form suitable for injection or infusion directly or after dispersion in or dilution with a physiologically acceptable carrier medium, e.g., water for injection. Thus the contrast agents may be formulated in conventional administration forms such as powders, solutions, suspensions, dispersions, and the like. However, solutions, suspensions and dispersions in physiologically acceptable carrier media will generally be preferred.

The contrast agents may be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Parenterally administrable forms, e.g., intravenous solutions, should of course be sterile and free from physiologically unacceptable agents, and should have low osmolality to minimize irritation or other adverse effects upon administration. Thus, the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the contrast agents and which will not interfere with the manufacture, storage or use of products.

The present invention includes one or more of the polymers of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, or the like.

Compositions suitable for parenteral injection may comprise physiologically acceptable sterile aqueous or nonaqueous solutions, dispersions, suspensions or emulsions and sterile powders and lyophilizates for reconstitution into sterile injectable solutions or dispersions. Examples of suitable aqueous and nonaqueous carriers, diluents, solvents or vehicles include water, ethanol, polyols (propyleneglycol, poly(ethylene glycol), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, cryoprotecting, and dispensing agents. Prevention of the action of microorganisms can be ensured by various antibacterial and antifungal agents, for example, parabens, chlorobutanol, sorbic acid, and the like. It may also be desirable to include isotonic agents, for example, sugars, sodium chloride and the like. In some embodiments, prolonged absorption of the injectable pharmaceutical form can be brought about by the use of agents delaying absorption, for example, aluminum monostearate and gelatin.

Exemplary Disclosure

The following examples illustrate the invention and is not to be construed as limiting of the specification and claims in any way.

Examples were prepared by the reaction of $\Omega$-methoxy-$\alpha$-amino poly(ethylene oxide) (PEO-NH$_2$) and $\Omega$-methoxy-$\alpha$-methylamino-poly (ethylene oxides) (PEO-NHCH$_3$), having molecular weights from 2000 to 10,000 with diethylenetriamine pentaacetic acid (DTPA) dianhydride in chloroform in the presence of a catalyst, 1,8-diazabicyclo-(5,4,0)-undec-7-ene. Complexation of the Gd$^{+3}$ ion was accomplished by adding excess GdCl$_3$ to the polymeric chelate composition in aqueous solution. Amount of complexation was determined by potentiometric titration of acid groups and by neutron activation or ICP-AES of Gd(157). Examples have the structure;

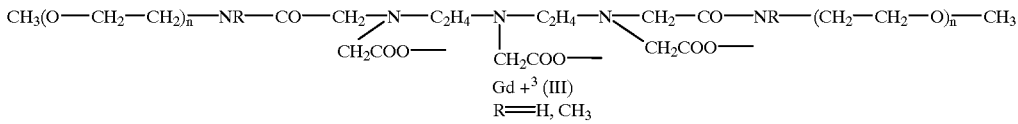

Gd $+^3$ (III)
R==H, CH$_3$

EXAMPLE 1

5 g of PEO-NH$_2$ (Sigma Chemical Co., St. Louis, Mo.) (5,000 MW) (1 mmol) was mixed with 0.178 g of DTPA dianhydride (Aldrich Chemical Co., Milwaukee, Wis.) (0.5 mmol) and 5 drops of the catalyst in 200 mL of chloroform. The mixture was refluxed at 60° C. for three days. The solvent from the reaction solution was removed by rotatory evaporator. The reaction product was then dissolved in water and acidified to pH 2.5 with concentrated HCl to convert any unreacted DTPA dianhydride to acid. The solution was exhaustively dialyzed in a 6000–8000 MW cut-off dialysis bag, followed by diafiltration using an Amicon® ultra filtration unit with 10K cut off filter, to remove any unreacted DTPA and PEO-NH$_2$. The DTPA-conjugated polymer was recovered by freeze drying, yielding 4.8 g solid. A sample of the solid polymer (MW$^-$11,000) was used to determine the number of acid groups per polymer chain. A pH titration was performed with the pre-complexed polymer to determine the composition of the polymeric chelate. The number of acid groups per polymer chain (MW$^-$11,000) was determined to be three, indicating that two PEO moieties were attached.

A small amount of the polymer was dissolved in water and mixed with three fold molar excess of GdCl$_3$. The solution was adjusted to pH 5.0 with NaOH and subjected to diafitration to remove excess GdCl$_3$, and the solid was recovered by freeze drying. The amount of Gd in the final complex was determined by neutron activation.

The neutron activation results in 0.01236 g Gd/g polymer compared to calculated value of 0.01427 g Gd/g polymer.

EXAMPLE 2

(A) 3.93 grams (0.01 mol.) of DTPA (pentaacetic acid form) was suspended in 4.85 mL of pyridine and 3.57 grams of acetic anhydride was added. The mixture was heated to 65° C. After cooling, the precipitate was filtered off and vacuum dried at 40° C., yielding 2.11 g. (87%) which was used unpurified in the next step.

(B) Ω-methoxyPEO tosylate (2000 MW) was suspended in 20 mL dioxane in a reaction bomb, cooled in an ice bath and methylamine bubbled into the mixture over 15 minutes. The bomb was sealed and heated to 160° C. in an oil bath for 18 hours. Upon cooling the solution was filtered and concentrated; the residual solid was dissolved in 40 mL of water +2.0 mls of 1N NaOH. The solution sat at room temperature for 30 minutes, and was extracted twice with chloroform; the extracts were dried over magnesium sulfate and concentrated in vacuo to a tan solid. Yield 1.54 g.

(C) The DTPA anhydride from example 2A and the Ω-methoxyPEO methylamine from example 2B are combined in 60 mL of chloroform and treated with six drops of 1,8-diazbicyclo[5.4.0]undec-7-ene DBU and heated in an oil bath at 60° C. for three days. The resulting product was concentrated in vacuo to yield 1.92 g. of a solid. The solid produced was dissolved in 55 mL of water, and diafiltered in a 200 mL Amicon diafiltration cell with a 5000 MW cut off membrane. Approximately 700 mL of diafiltrate was collected. The retentate was filtered through a 0.2 micron filter and concentrated in vacuo at 1.5 torr and freeze dried to yield 1.183 g polymer solid.

(D) The product in example 2C was dissolved in 100 mL of water containing 0.698 g. of GdCl$_3$.6H$_2$O. The yellow solution was stirred at room temperature for 1 hour and then was placed in a 200 ml. Amicon diafiltration cell with a 5000 MW cut-off membrane and diafiltered with water. 725 ml of diafiltrate was collected, and the yellow retentate was filtered through a 0.2 micron filter and freeze dried; yield 3.48 g; 4.38% Gd by ICP analysis.

EXAMPLE 3

(A) Ten grams of Methoxy(PEO-OH(5000 MW) in 100 mL pyridine was combined with a mixture of 4.0 g. of tosyl chloride and 4.1 g of 2,6-di-t-butyl-4-methylpyridine in 10 mls of pyridine. The resulting solution was stirred at room temperature under nitrogen for 5 hours, then poured into a mixture of 100 mls of concentrated HCl and ice, extracted twice with chloroform and dried over magnesium sulfate and concentrated in vacuo to a white solid which was triturated overnight in ether. The solid was filtered, washed with ether, and vacuum dried to 9.79 g (95%) of the desired product. The resulting tosylate was then aminated as in Example 2B with methyl amine.

(B) 0.293 g. of DTPA anhydride was combined with Ω-methoxy methylamino PEO (9.79 g.) in 390 mL of 1,2 dichloroethane and 10 drops of DBU was added dropwise the mixture was heated in oil bath at 60° C. under nitrogen for three days. The reaction mixture was cooled to room temperature, concentrated in vacuo to 10.42 g of a tan yellow solid which was taken up in 180 mL of water, filtered, and placed in a 200 mL Amicon diafiltration cell with a 10,000 molecular weight cut-off membrane, and diafiltered with water at room temperature. Diafiltration was stopped after 1150 mL of diafiltrate was collected, and the retentate was freeze dried to yield 5.39 g of an off-white fluffy solid of approximately 10,000 molecular weight.

(C) 2.00 g of the product of example 3b was dissolved in 50 mL of water and 0.132 g GdCl$_3$ hexahydrate was added. The solution was stirred at room temperature for one hour followed by diafiltration in a 200 mL Amicon diafiltration cell (5000 MW cut-off membrane) versus water. After collecting 700 mL of diafiltrate, the retentate was filtered and freeze dried to yield 1.81 g of product as a fluffy white solid of approximately 10,000 mol. weight; 1.18% Gd by ICP analysis.

EXAMPLE 4

MethoxyPEO—OH (molecular weight 10,000) was aminated using the method of example 2B and then reacted with DTPA anhydride according to the method of example 2C. This material (4.12 g) was dissolved in 100 mL of water containing 0.149 g of GdCl$_3$ hexahydrate and stirred at room temperature for one hour, followed by diafiltration, yielding 4.106 g of a fluffy white solid; 0.763% Gd by ICP analysis.

EXAMPLE 5

(A) It is contemplated that a chelating residue comprising two DTPA residues is prepared by reacting the free carboxylic acid of DTPA anhydride with carbonyl N,N$^1$-dimethylimidazolium ditriflate at reduced temperature in an inert atmosphere followed by treatment with ethylene diamine to provide a tetraanhydride diamide.

(B) The resulting anhydride from 5A is then reacted with methoxy PEGamine according to the method of Examples 1–3 to form a polymer of Formula I.

EXAMPLE 6

(A) It is contemplated that a chelating agent comprising three DTPA residues is prepared by reacting DTPA dianhydride with carbonyl N,N$^1$-dimethyldrimidazolium ditriflate as above followed by treatment with diethylene triamine to provide a hexaanhydride triamide.

(B) The resulting anhydride from 6A is then reacted with methoxy PEG amine according to the method of Examples 1 to 3 to form a polymer of formula I.

Each of the examples 1 through 4 were tested for blood pool retention time in rodents, against MAGNEVIST, DTPA/Gd$^{+3}$, a known imaging compound. Retention time in the chart below is reported as the blood pool half life, T ½ minutes) for half of the composition to be depleted from the blood pool.

|  | MW of Composition | Blood Pool T½ (Minutes) |
| --- | --- | --- |
| (Magnevist ®) | 0.9K | 12 |
| 2 | 4.5K | 15.6 |
| 3 | 11K | 15.3 |
| 4 | 21K | 82.9 |

We claim:

1. A segmented polymer having a molecular weight of at least 4500 and the formula

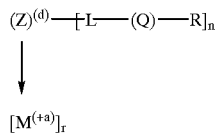

wherein:

Z is a chelating residue;

Q is a divalent poly(alkylene oxidylene) moiety having a carbon terminus at R and at L;

L represents an amide linkage;

E$^{(b)}$ is one or more counterions each having a charge of b;

b is an integer from 1, 2 and 3;

n is an integer selected from the group 2, 3 and 4;

w is zero or an integer from 1 to 5;

M$^{(+a)}$ is a cation, having a charge of +a;

a is an integer from 1 to 4;

r is 0 or an integer from 1 to 3, provided that when r is 2–3, each M$^{(+a)}$ can be the same or different cation;

d is the total charge on the chelating residue and is an integer from 0 to 10;

d+Σ(b·w)+Σ(a·r)=0; and

R is a capping moiety chosen from the group consisting of hydrogen, hydroxyl, C$_1$–C$_4$ alkyl, aryl containing 6 to 24 carbon atoms, C$_2$–C$_5$ alkanoyloxyl and C$_1$–C$_4$ alkoxy, or R is an immunoreactive group or cytotoxic drug linked to Q by a chemical bond or a linking group.

2. The polymer of claim 1 wherein said composition has a molecular weight of 10,000 to 40,000.

3. The polymer of claim 2 wherein r is one to three and each cation is a paramagnetic ion.

4. The polymer of claim 2 wherein the chelating residue consists of one or more units of DTPA.

5. The polymer of claim 3 wherein Q is a poly(ethylene oxidylene) moiety.

6. The polymer of claim 3 wherein M$^{(+a)}$ is selected from the group consisting of Gd$^{+3}$, Fe$^{+3}$, Mn$^{+2}$, Mn$^{+3}$, Dy$^{+3}$ and Cr$^{+3}$.

7. A polymer according to claim 1 wherein R is an immunoreactive group, r is at least 1, and [M$^{+a}$] is a cation selected from the group consisting of a radionuclide ion, a fluorescent metal ion, and a paramagnetic ion.

* * * * *

UNITED STATES PATENT AND TRADEMARK OFFICE
CERTIFICATE OF CORRECTION

PATENT NO.      : 6,017,522
DATED           : JANUARY 25, 2000
INVENTOR(S)     : DENNIS E. BUTTERFIELD et al.

It is certified that error appears in the above-identified patent and that said Letters Patent is hereby corrected as shown below:

On the TitlePage, Col. 1, replace "[73] Assignee: Sterling Winthrop Inc., New York, N.Y." with --[73] Assignee: Nycomed Imaging AS, Oslo, Norway--.

Signed and Sealed this

First Day of May, 2001

Attest:

NICHOLAS P. GODICI

*Attesting Officer*    *Acting Director of the United States Patent and Trademark Office*